United States Patent [19]

Cahalan et al.

[11] Patent Number: 5,607,475
[45] Date of Patent: Mar. 4, 1997

[54] BIOCOMPATIBLE MEDICAL ARTICLE AND METHOD

[75] Inventors: Linda L. Cahalan; Patrick T. Cahalan, both of Geleen; Michel Verhoeven, Maastricht; Marc Hendriks, Hoensbroek; Benedicte Fouache, Maastricht, all of Netherlands

[73] Assignee: Medtronic, Inc., Minneapolis, Minn.

[21] Appl. No.: 518,129

[22] Filed: Aug. 22, 1995

[51] Int. Cl.$^6$ ................................. A61F 2/02; A61F 2/06
[52] U.S. Cl. ................................. 623/11; 623/1; 424/422; 424/423; 427/2.24
[58] Field of Search ................................. 623/1, 7, 12, 11; 606/194, 195; 427/2.1, 2.24, 2.25; 424/422, 423, 424; 525/54.1

[56] References Cited

U.S. PATENT DOCUMENTS

| | | |
|---|---|---|
| 3,549,409 | 12/1970 | Dyck. |
| 3,585,647 | 6/1971 | Gajewski et al.. |
| 3,639,141 | 2/1972 | Dyck. |
| 3,826,678 | 7/1974 | Hoffman et al.. |
| 4,118,485 | 10/1978 | Eriksson et al.. |
| 4,138,382 | 2/1979 | Polmanteer ................................. 623/7 |
| 4,356,433 | 10/1982 | Linden. |
| 4,378,435 | 3/1983 | Takagi et al.. |
| 4,521,564 | 6/1985 | Solomon et al.. |
| 4,526,714 | 7/1985 | Feijen et al.. |
| 4,539,061 | 9/1985 | Sagiv. |
| 4,565,740 | 1/1986 | Golander et al.. |
| 4,600,390 | 7/1986 | Gobel et al.. |
| 4,600,652 | 7/1986 | Solomon et al.. |
| 4,613,665 | 9/1986 | Larm. |
| 4,634,762 | 1/1987 | Feijen et al.. |
| 4,642,242 | 2/1987 | Solomon et al.. |
| 4,673,584 | 6/1987 | Nygren et al.. |
| 4,720,512 | 1/1988 | Hu et al.. |
| 4,786,556 | 11/1988 | Hu et al.. |
| 4,886,062 | 12/1989 | Wiktor. |
| 5,018,829 | 5/1991 | Ogawa ................................. 350/96.34 |
| 5,030,610 | 7/1991 | Wogoman. |
| 5,032,666 | 7/1991 | Hu et al.. |
| 5,049,403 | 9/1991 | Larm et al.. |
| 5,053,048 | 10/1991 | Pinchuk. |
| 5,112,640 | 5/1992 | Warunek et al.. |
| 5,132,108 | 7/1992 | Narayanan et al.. |
| 5,133,732 | 7/1992 | Wiktor. |
| 5,229,172 | 7/1993 | Cahalan et al.. |
| 5,308,641 | 5/1994 | Cahalan et al.. |
| 5,344,455 | 9/1994 | Keogoh et al.. |
| 5,356,435 | 10/1994 | Rowland et al.. |
| 5,415,938 | 5/1995 | Cahalan et al.. |

FOREIGN PATENT DOCUMENTS

| | | |
|---|---|---|
| 1319007 | 5/1973 | United Kingdom. |
| 2023022 | 12/1979 | United Kingdom. |

OTHER PUBLICATIONS

Jnl. of Chromatography, 107 (1975) 402–406 "Chemically bonded phases for liquid chromatography . . . " by B. B. Wheals.

Anal Chem. 1993, 65, 822–826, "Horizontal Polymerization of Mixed Trifunctional . . . " by Wirth and Fatunmbi.

Silicon Compounds: Register and Review, Huls America Inc. 5th edition, "Silane Coupling Agent Chemistry" by Arkles.

Jnl. of Polymer Science: Polymer Phsics Ed., vol. 18, No. 9, Sep. 1980, "Silane Coupling Agents", by Ishida and Koenig.

Jnl. Applied Polymer Science, vol. 47, No. 3, Jan. 1993, "Surface Graft Polymerization of Ionic . . . " by Uchida, Uyama and Ikada.

Jnl. Polymer Science, vol. 30, No. 4, Mar. 1992, "Grafting of Polymers onto Carbon Whisker by Anionic . . . " by Tsubokawa, Yoshihara and Sone.

Polymer Jnl. vol. 24 No. 1, 1992, "Study of Blood Compatible Polymers . . . " by Matthew and Kodama.

Jnl. of Applied Polymer Science, vol. 44, No. 4, Feb. 1992, "Graft Polymerization of Vinyl . . . " by Browne, Chaimberg and Cohen.

Langmuir The ACS Jnl of Surfaces and Colloids, Sep. 1993, vol. 9 No. 9, "Structure and Tribological Properties of . . . " by Ruhe, Novotny, Kanazawa, Clarke and Street.

Langmuir The ACS Jnl of Surfaces and Colloids, Aug. 1991, vol. 7, No. 8, "Silanation of Silica Surfaces. A New Method . . . " by Silberzan, Leger, Ausserre and Benattar.

Inst. of Chemical Process Fundamentals, Czech. Acad. of Sciences, Prague, Czech., "Some Applications of Carbon-Functional Organosilicon Compounds", by Vaclav Chgvalovsky.

"Materials for enhancing cell adhesion by immobilization of cell–adhesive peptide" by Y. Ito et al. from Journal of Biomedical Materials Research, vol. 25, 1325–1337 (1991).

*Primary Examiner*—John G. Weiss
*Assistant Examiner*—Francis K. Cuddihy
*Attorney, Agent, or Firm*—Daniel W. Latham; Harold R. Patton

[57] ABSTRACT

A medical article having a metal or glass surface with the surface having an adherent coating of improved biocompatibility. The coating is made by first applying to the surface an silane compound having a pendant vinyl functionality such that the silane adheres to the surface and then, in a separate step, forming a graft polymer on the surface with applied vinylsilane such that the pendant vinyl functionality of the vinylsilane is incorporated into the graft polymer by covalent bonding with the polymer. Biomolecules may then be covalently attached to the base layer.

12 Claims, No Drawings

BIOCOMPATIBLE MEDICAL ARTICLE AND METHOD

BACKGROUND OF THE INVENTION

The present invention generally relates to medical devices for implantation in a human or animal body which are provided with improved tissue and blood biocompatibility. More specifically, metal or glass portions of the medical device are provided with a surface which has been chemically modified with covalently attached bioactive molecules.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body.

As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" which can promote the attachment and growth of a normal cell or protein layer such that the body accepts the device as a normal part of the body. Biomolecules such as growth factors and cell attachment proteins which have been attached to the device surface could be used for this purpose. In addition, biomolecules such as antithrombogenics, antiplatelets, anti-inflammatories and the like have also been used to improve the biocompatibility of surfaces.

A number of approaches have been suggested to attach such biomolecules. One such approach is set forth in Dekker et al., "Adhesion of endothelial cells and adsorption of serum proteins on gas plasma-treated polytetrafluoroethylene", Biomaterials, vol. 12 Mar. 1991. In that approach, PTFE substrates were modified by radio frequency plasma to improve the wettability of the surface. Human serum albumin, human fibronectin, human immunoglobulin and human high-density lipoprotein were adsorbed to the plasma-treated substrates followed by seeding with human endothelial cells. Another approach is described in U.S. Pat. No. 5,055,316 to Hoffman et al in which serum proteins such as albumin, immunoglobulins, fibrinogen or fibronectin, or proteins from different sources such as protein-A or glycoproteins are bound to a surface by first using plasma gas discharge in the presence of a plasma-polymerizable fluorinated hydrocarbon gas to provide a plasma-deposited surface, followed by exposure to a solution of the protein. Covalent attachment of such biomolecules can be found in Ito et al., "Materials for Enhancing Cell Adhesion by Immobilization of Cell-Adhesive Peptide", Journal of Biomedical Materials Research, 25:1325–1337 (1991) in which fibronectin or RGD peptide are bonded to the hydrogel by the use of a water soluble carbodiimide. Although this method allows coupling of the biomolecule extended from the surface, the fact that the biomolecule is immobilized throughout the gel layer reduces the availability of the biomolecule for interaction with, for example, cells intended to adhere to the biomolecule.

Spacer molecules have been used to address this problem. A spacer molecule is a molecule or compound which is capable of attachment to a solid surface, is large enough to extend from the surface of said surface and is capable of immobilizing a biomolecule and/or biomolecules. The spacer insures that the active site of the biomolecule is held outward away from the support so as to contact the body fluid efficiently. The spacers are derived from organic molecules having at least two reactive functional groups, or more, generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radio frequency plasma treatment by subjecting it to a radio frequency electric field in the presence of a water vapor plasma medium. An aqueous solution of polyethyleneimine (PEI) and 1-(3-dimethylpropyl)-3-carbodiimide (EDC) coupling agent was applied to the radio frequency plasma discharge modified polyurethane surface. An aqueous solution of heparin and EDC was then applied to the PEI-treated surface in order to provide a polymeric surface having an antithrombogenic agent secured to its surface. However, considering the heterogeneity of the polyurethane surface even coating with the multi-functional spacer molecule is not guaranteed.

Additional coverage can be provided, for example, according to U.S. Pat. No. 4,565,740 to Colander et al. or U.S. Pat. No. 5,049,403 to Larm et al. In the first of these patents, a complex of a polymeric cationic surfactant (e.g. a polyalkyleneimine) and a dialdehyde (e.g. glutaraldehyde) is adsorbed onto a substrate material. In the second of these patents, a polyamine is adsorbed onto the surface of a substrate and crosslinked with crotonaldehyde. Multiple coatings, including intermediate layers of anionic material are then applied to obtain an effective coating. However, these crosslinked coatings rely on adsorption onto the surface and ionic bonding to the surface, which may not provide good bonding of the coating to the surface.

The inventors of the present invention have contributed to improvements in biocompatibility of biomaterials through the use of multilayer coatings in their U.S. Pat. Nos. 5,229,172; 5,308,641 and 5,350,800. For example, in U.S. Pat. No. 5,229,172, we discovered a method for modifying the surface characteristics of a polymeric material by providing a base layer of grafted acrylamide on the polymeric surface which can be used to attach various spacers and biomolecules. Or, in U.S. Pat. No. 5,308,641, we discovered an improved spacer material which includes a polyalkyeneimine covalently attached to an aminated substrate and crosslinked with a crosslinking agent which is difunctional in aldehyde groups. Or, in U.S. Pat. No. 5,350,800, we discovered a method for attaching a biomolecule having carboxyl groups to an aminated solid surface by a carbodiimide and then selectively restoring the bio-functionality of the carboxyl groups.

On metal or glass surfaces, the binding of the base layer of such multi-layer coatings can be a problem since there is no organic structure to provide covalent bonds between the metal or glass substrate and the grafted base layer. Others have addressed the problem of binding to metals and glass by applying aminosilanes to adhere to the surface and then attaching the biomolecule to the aminosilane through the amine functionality of the aminosilane. This can be seen in U.S. Pat. No. 5,355,433 issued to Rowland et al in which an aminosilane is used to adhere a heparin molecule to an oxidized tantalum surface. Aminosilanes are also disclosed for attachment of a heparin molecule to glass or metal surfaces in U.S. Pat. No. 4,118,485 issued to Eriksson et al. However, the use of aminosilanes in coatings of this sort has not been very good in producing a surface with a high level of both bioeffectiveness and stability.

It is therefore an object of the invention to provide a base for the attachment of biomolecules and/or spacer molecules with improved stability on metal or glass substrates.

It is also an object of the invention to provide a combined base/spacer which presents a stable platform for the attachment of the biomolecule and thereby prevents the attached biomolecule from being buried in the spacer layer.

SUMMARY OF THE INVENTION

The present invention therefore includes a medical article having a metal or glass surface with the surface having an adherent coating. The coating includes a silane compound having a vinyl functionality such that the silane adheres to the surface with the vinyl functionality pendant from the surface and then forming a graft polymer on the surface with applied silane such that the pendant vinyl functionality of the silane is incorporated into the graft polymer by covalently bonding it to the graft polymer.

The preferred silane is generally a compound of the structure $$C_2H_3—Si—X_3$$

where X is a halogen, methoxy or ethoxy groups. Compounds of this type include the preferred compound trichlorovinylsilane. Other silanes can also be used as set forth in greater detail below.

The base layer which incorporates the vinyl functionality of the silane also includes a thin but densely formed graft polymer. Preferably, the graft polymer is formed by free radical reaction from an ethylenically unsaturated monomer. Thus the reaction which forms the graft polymer also activates the pendant vinyl group of the silane and incorporates it into the graft polymer during its formation. An oxidizing metal such as ceric ion can be used to initiate the polymerization reaction. Ceric ion grafting is known to work best when the monomer does not have a tendency to precipitate with the ceric ion, for instance, when used with acrylamide. Acrylic acid is also a good candidate monomer for use with ceric ion grafting provided that polymerization inhibitors present in commercial supplies of acrylic acid are first removed by distillation. Blends of acrylic acid, acrylamide and other monomers can also be used depending on the desired properties of the graft.

The biofunctional molecules attached to grafted surfaces can be biomolecules such as anticoagulants (e.g. heparin, heparin sulfate, dermatan sulfate, glycosaminoglycan sequences and analogs, hirudin, thrombin inhibitors), thrombolytic agents (e.g. streptokinase, tissue plasminogen activator), procoagulant agents, platelet adhesion inhibitors, platelet activity inhibitors, cell attachment proteins, growth factors/cytokines, wound healing agents, antimicrobial agents, anticancer agents, hormones, analgesics, detoxification agents and the like. These biomolecules can be covalently bonded to the grafted surface by pendant functional groups such as amine and carboxyl groups in the grafted polymer which are reacted with corresponding groups on the biofunctional molecules according to methods which are well known by those skilled in the art.

Preferably, a medical article according to the present invention includes a spacer as a means for attachment for the biomolecule. Such spacers are well known in the art as set forth above in the background of the invention. A preferred spacer can be a polyamine spacer as set forth in our U.S. Pat. No. 5,308,641 which is hereby incorporated by reference in its entirety. Examples of devices which may be provided with biocompatible surfaces in accordance with this invention include prosthetic devices and components of implanted prosthetic devices such as in vascular grafts or hard tissue prosthetics, invasive devices such as indwelling catheters or in devices for extracorporeal blood handling such as dialysis equipment or blood circulation or oxygenation equipment used in cardiovascular surgery. In a particular vascular prosthesis embodiment of the invention, the base layer described above can be attached to a metallic medical device which undergoes movement during implantation and/or use, since the bioactive coating is able to withstand flexure without cracking or delamination. Exemplary in this regard are metallic radially expandable generally tubularly shaped endoprostheses which are generally known as stents. An exemplary stent in this regard is described in U.S. Pat. Nos. 4,886,062 and 5,133,732 issued to Wiktor, the subject matter thereof being incorporated by reference. Stents such as these are made of very fine gauge metallic wire, typically tantalum wire or stainless steel wire. During implantation, these stents are mounted onto the balloon of an angioplasty catheter or the like until a partially occluded location along a blood vessel or the like is reached, at which time the balloon and the stent are radially and circumferentially expanded for purposes of opening the occlusion and supporting the vessel at that location. This necessarily involves rather extensive bending of the tantalum wire. Many coatings do not have the flexibility and/or adherence properties which are needed to avoid cracking and/or loss of the coating when subjected to this type of flexure. Further, a stent provided with heparin as a biomolecule according to the present invention and implanted within a blood vessel can prevent thrombus formation on the metallic member that may otherwise occur as a result of the stent implantation procedure.

DETAILED DESCRIPTION OF THE INVENTION

The base layer of the multilayer coating is made by first applying to the surface a silane having a pendant vinyl functionality such that the silane adheres to the surface. The silane used includes compounds of the structure $$C_2H_3—Si—X_3$$

or, optionally

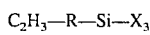

where X is a halogen, methoxy or ethoxy group, and R is a short chain alkyl group. A preferred silane compound is trichlorovinylsilane.

Those skilled in the art will recognize that the successful application of the silane to a surface includes precleaning of the surface and the control of moisture at the surface during application of the silane. Multistep cleaning and drying operations are therefore used to provide a clean surface and to control moisture. An exemplary method for cleaning and drying can be found herein in the examples.

The base layer which incorporates the vinyl functionality of the silane includes a thin but densely formed graft polymer. Preferably, the graft polymer is formed by free radical reaction from an ethylenically unsaturated monomer. Thus the reaction which forms the graft polymer also activates the pendant vinyl group of the silane and incorporates it into the graff polymer during its formation. An oxidizing metal such as ceric ion can be used to initiate the polymerization reaction.

The preferred grafting process is carried out on the substrate in an aqueous solution (20 to 40 wt % of monomer) as contrasted with other solvent polymerization processes such as organic solvent polymerization or even bulk polymerization. The composition of the preferred monomer solution is predominantly acrylic acid and acrylamide in order to provide a desired density of carboxyl groups on the grafted surface which can be used to attach the biomolecule or a spacer layer. Alternatively, acrylamide can be used exclusively followed by hydrolysis treatment on the resulting polymer to provide the desired density of carboxyl groups.

The grafting reaction of the present invention may be carried out at temperatures between about 18° C. and 25° C. The present invention may be carried out under pressure or under partial vacuum, but it is preferred to utilize atmospheric pressure inasmuch as the reaction proceeds very favorably at this pressure. The pH of a grafting solution with ceric ammonium nitrate is typically about 1.4.

The amount of ceric ion utilized in the practice of the process of the present invention can be varied over fairly wide limits. For example, one may utilize from about 0.0001 to 0.002 mole of ceric ion per mole of polymerizable monomer. Preferably one would use between 0.0002 to 0.0005 mole of ceric ion per mole of acrylamide. Ceric ion is preferably introduced into the reaction mixture in the form of a ceric salt. Among the cerium salts adapted for use in the present invention are ceric nitrate, ceric sulfate, ceric ammonium nitrate, ceric ammonium sulfate, ceric ammonium pyrophosphate, ceric iodate, ceric salts of organic acids, such as cerium naphthenate and cerium linoleate and the like. These compounds may be employed singly or in combination with one another.

In general, the time required to achieve a desired degree of polymerization may be determined empirically. Thus, for example, acrylamide may be grafted at different time intervals and the extent of grafting determined by staining of functional groups introduced in the graff by chemical modification. The length of the polymeric chain and graft density may be varied by varying the acrylamide concentration, ceric ion concentration, temperature and oxygen concentration.

Biofunctional molecules (biomolecules) such as anticoagulants (e.g. heparin, heparin sulfate, dermatan sulfate, glycosaminoglycan sequences and analogs, hirudin, thrombin inhibitors), thrombolytic agents (e.g. streptokinase, tissue plasmogen activator), procoagulant agents (e.g. Factor VIII, von Willebrand's Factor, collagen), platelet adhesion inhibitors (e.g. albumin, albumin adsorbing surfaces, hydrophilic hydrogels, phospholipids), platelet activity inhibitors (e.g. aspirin, dipyrimadole, forskolin), cell attachment proteins (fibronectin, vitronectin, different collagen types, laminin, elastin, basement membrane proteins, fibrin, peptide sequences), growth factors/cytokines (e.g. transforming growth factor, basic fibroblast growth factor, platelet derived growth factor, endothelial cell growth factor, gamma interferon), hydrogels, collagens, epidermal growth factor, antimicrobial agents (e.g. gentamicin, rifampin, silver salts), anticancer agents (e.g. 5-fluorouracil), hormones (insulin, vasopressin progesterone, human growth hormone), analgesics, detoxification agents (e.g. chelating agents) and the like can be ionically or covalently bonded to a metallic substrate by first applying the grafting method of the present invention to provide a suitable surface to which to attach the biomolecule. Such molecules can be covalently attached to a grafted surface made according to the present invention in which pendant functional groups such as amine and carboxyl groups introduced in the gel by chemical modification are reacted with corresponding groups on the biofunctional molecules according to methods which are well known by those skilled in the art.

Preferably, a medical article according to the present invention includes a spacer molecule as a means for attachment for the biomolecule. Such spacer molecules are well known in the art as set forth above in the background of the invention. The preferred spacer molecule is a polyalkyleneimine or other branched polyamines. By polyalkyleneimine we therefore mean to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkyleneimines employed in the present invention are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used in the present invention.

A crosslinking agent can be employed in the present invention in order to provide additional stability of the polyamine spacer. The crosslinking agent can be any crosslinking agent which is at least difunctional in groups which are reactive with the amine groups present in the polyamine spacer. The crosslinking agent may therefore have an aldehyde functionality. For example, glutaraldehyde, crotonaldehyde, goxal, maonaldehyde, succinaldehyde, adipaldehyde, and dialdehyde starch could be used. Other suitable crosslinking agents are cyanuric chloride and derivatives, divinyl sulfone, epoxy compounds, imidate esters and other crosslinking agents reactive toward amines.

The spacer of the present invention can therefore be made by applying a polyalkyleneimine to the grafted surface and then treating the applied polyalkyleneimine with the crosslinking agent. Preferably, the crosslinking agent used to crosslink the polyalkyleneimine is applied in dilute solution and at a suitable pH to accomplish light crosslinking. For example, an aldehyde solution that has a concentration in the range of about 0.0005M to about 0.05M could be used while a concentration in the range of about 0.0005M to about 0.005M would be preferred. Also, for example, a pH for the aldehyde solution in the range of about 7 to about 10 would be preferred. The time required to complete the light crosslinking reaction is typically just a few minutes in the case of dialdehydes or longer times for other crosslinkers.

Preferably, the crosslinking reaction with the polyamine is undertaken before applying it to the grafted surface.

The polyalkyleneimine is covalently bonded to the grafted surface by contacting the grafted surface with an activating agent which will activate the carboxyl groups on the grafted surface and cause them to bind to the polyalkyenelimine. The covalent bonding agent used is preferably a water soluble carbodiimide of the structure $R_1N=C=NR_2$ where $R_1$ can be an alkyl or cycloalkyl group and $R_2$ can be an alkylamine or cycloalkylamine group such as 1-ethyl-3-(3-dimethyl-aminopropyl)carbodiimide hydrochloride, or 1-cyclohexyl-3-(2-morpholinoethyl)carbodiimide. The reaction with the carbodiimide is undertaken in a cold solution (0°–4° C.) at a pH of about 5 although a room temperature reaction is also acceptable. The grafted surface can be pretreated with the carbodiimide and then contacted with the polyamine or, preferably, the grafted surface can be coated with the polyamine and then treated with the carbodiimide. Preferably, the polyamine and carbodiimide are previously mixed together at a pH of approximately 9 before applying to the graft. In the reaction, the carbodiimide activates the carboxyl groups of the graft after reaction with the polyamine which leads to the formation of a suitable amide bond, resulting in effective immobilization of the polyamine on the grafted surface.

The immobilized polyamine can then be used as a platform for the immobilization of various biofunctional molecules. For example, in the case of heparin, the heparin can be modified to contain a reactive aldehyde moiety which does not inhibit the bioactivity of the heparin but does react with the amine groups of the polyamine to covalently attach the heparin to the polyamine in the presence of a suitable reducing agent such as $NaCNBH_3$. The aldehyde groups can be formed on heparin by controlled periodate oxidation. Part of the saccharide molecules in the heparin contain unsubstituted glycol structures (c(2)-OH AND C(3)-OH), which react with periodatem splitting the C(2)–C(3) bond, generating a dialdehyde structure and leaving the polysaccharide main chain intact. After oxidation (under the exclusion of light) the solution containing the activated heparin can be diluted into a proper buffer to a suitable concentration. The solution is then applied to the polyamine immobilized on the surface. The aldehyde functional groups on the heparin are then reacted with the free amine groups to give a Schiff base formation that may be reduced to provide stable secondary amines. Exemplary reducing agents include sodium borohydride, sodium cyanoborohydride, dimethylamine borane and tetrahydrofuran-borane. Upon completion of the coupling reaction, the surface may be washed with water and solutions of sodium chloride to remove loosely bound or unreacted heparin.

EXAMPLE 1

A piece of coiled tantalum wire was ultrasonically cleaned in 2% Micro-clean for 30 minutes followed by ultrasonic treatment in deionized water for 30 minutes. This last step was repeated after which the coil was rinsed in isopropanol and dried at 50° C. for 20 minutes.

The cleaned coil was swirled in a 2% solution of trichlorovinylsilane (Merck Darmstadt, FRG) in xylene for 60 seconds followed by rinsing for 60 seconds in xylene, 60 seconds in isopropanol, 60 seconds in water and finally in acetone. The coil was then allowed to air dry overnight.

The dried coil was then placed into a glass tube which was filled with 15 ml of an aqueous solution of 35 wt % of freshly distilled acrylic acid and 5 wt % acrylamide. To the 15 ml of monomer solution, 0.9 ml of a solution of ceric ammonium nitrate (0.1M) in nitric acid (0.1M) was added. Deaeration was performed for 3–5 minutes at about 18 mm Hg followed by ultrasonic treatment for 10 minutes and an additional incubation of 35–40 minutes, all at room temperature. The grafted samples were then rinsed 10 times with deionized water at 50° C. followed by an overnight incubation at 50° C. Samples taken showed a deep stain when soaked in toluidine blue solution.

A solution of 375 ml crotonaldehyde in 0.1M sodium borate (pH=9.1) was made and after 10 minutes stirring polyethyleneimine (PEI, Polymin SN from BASF with a $M_w$ of 60,000) was added. After an additional mixing of 5 minutes, the coil was incubated in the crosslinked PEI solution for one hour while shaking. After rinsing with deionized water, the coil was contacted with a solution of 0.5 wt % PEI (Polymin SN) in 0.1M sodium borate (pH=9.1) for 10 minutes. Water soluble carbodiimide (1-(3-diethylaminopropyl)-3-ethylcarbodiimide.HCl) at a concentration of 0.05M was added. Coupling was allowed to proceed for one hour while shaking followed by rinsing with deionized water for 10 minutes.

Oxidized heparin was prepared by adding 0.165 mg $NaIO_4$/ml to 5 mg native heparin (Akzo)/ml 0.05M phosphate buffer (pH=6.88; 0.025M $K_2HPO_4$+$NaH_2PO_4*2H_2O$) under the exclusion of light. After overnight oxidation, the resulting heparin solution was diluted in 0.4M acetate pH=4.6 at a ratio of 1:20. 0.1 mg of $NaCNBH_3$/ml was added to the diluted heparin and the coil was incubated in this solution for 2 hours at 50° C. After rinsing with deionized water, 1M NaCl and water again to remove loosely bonded heparin, the coil was incubated with toluidine blue which provided an even lilac stain, indicating successful heparinization. An additional bioactivity test was also successfully performed to determine the ability of the heparinized surface to deactivate thrombin via activation of previously adsorbed antithrombin III. The bioactivity was also tested successfully after an overnight challenge with 1% sodium dodecylsulfate at 50° C. indicating excellent stability of the coating on the metal substrate.

COMPARATIVE EXAMPLES 2–8

Comparative tests were conducted on a variety of variables. Different methods to aminate the metal surface and their ability to bind heparin via the reductive amination process described in Example 1 were evaluated. Variables tested included the use of no silane, an aminosilane, aminopropyl triethoxysilane (APTES), and a vinylsilane, trichlorovinylsilane (TCVS); the use of grafted polymers (acrylamide (AAm) and acrylic acid (Ac)) and copolymers as a base layer; adsorbed or grafted PEI layer; and various crosslinkings of the PEI layer (crotonaldehyde (Ca), glutaraldehyde (Gda) and divinylsulfone (DVS)). For Example 8, coils were prepared with a grafted hydrogel essentially as described in Example 1. A solution of 0.1 wt % PEI (Polymin SN from Basf with a $M_w$ of 60,000) in 0.1M borate pH=9.0 was prepared to which water soluble carbodimide (1-(3-dimethylaminopropyl)-3-ethylcarbodiimide.HCl, Aldrich) up to a concentration of 0.05M was added. Immediately after dissolution of the carbodiimide, the grafted coils were contacted with the solution for 50 minutes while gently shaking. After copious rinsing with water, heparin was coupled to the coils as described in Example 1. The test results for Examples 2–8 are given below in Table 1.

TABLE 1

| Example | Silane | Process | PEI Layer | Bioactivity | Staining |
|---|---|---|---|---|---|
| 2 | None | Adsorbed | Basf/Ca | 0.0465 | 0 |
| 3 | APTES | Adsorbed | Basf/Ca | 0.0864 | 0 |
| 4 | APTES | Adsorbed | Fluka/DVS | 0.1512 | 0 |
| 5 | APTES | Adsorbed | Fluka/Gda | 0.0090 | 0 |
| 6 | TCVS | Graft/Ac | Basf/Ca | 0.2192 | 4 |
| 7 | TCVS | Graft Ac + AAm | Basf/Ca | 0.330 | 4+ |
| 8 | TCVS | Graft Ac + AAm | Basf | 0.323 | 4+ |

The comparative test results in Table 1 indicate that the bioactivity of the adsorbed PEI layer (in IU of DEA/cm$^2$) was less than that for a covalently bonded layer as present in Examples 7 and 8. Further, the staining following the overnight challenge with 1% sodium dodecylsulfate (on a scale of 0=no stain to 5=dark stain) showed that the heparin layer was not effectively maintained on test samples with the aminosilane and adsorbed PEI whereas the heparin layer was retained on the covalently bonded PEI.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. An endoprosthesis having a metal surface contacting body fluids, the metal surface having a coating thereon comprising:
   (a) a silane which includes a vinyl functionality, the silane adherent to the metal surface such that the vinyl functionality is pendant from the surface;
   (b) a graft polymer, the graft polymer covalently bonded with the pendant vinyl functionality of the adherent silane, the graft polymer simultaneously formed and bonded to the pendant vinyl functionality by free radical reaction initiated by an oxidizing metal with at least one ethylenically unsaturated monomer selected from the group consisting of acrylamide and acrylic acid;
   (c) a polyamine spacer covalently attached to the graft polymer; and
   (d) a biomolecule covalently attached to the spacer.

2. The endoprosthesis of claim 1, wherein the silane includes a functional group selected from the group consisting of halogen, methoxy and ethoxy groups.

3. An endoprosthesis as in claim 2, in which the silane is trichlorovinylsilane.

4. An endoprosthesis as in claim 1, in which the polyamine spacer is a polyalkyleneimine.

5. An endoprosthesis as in claim 1, in which the biomolecule is an antithrombotic.

6. An endoprosthesis as in claim 5, in which the antithrombotic is selected from the group consisting of heparin and heparin derivatives.

7. An endoprosthesis having a metal surface contacting body fluids, the metal surface having a coating thereon comprising:
   (a) a silane having the structure

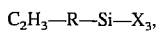

$$C_2H_3-R-Si-X_3,$$

wherein X is a halogen, methoxy or ethoxy group and R is an optional short chain alkyl group, the silane adherent to the metal surface such that the vinyl functional group is pendant from the surface;
   (b) a graft polymer, the graft polymer covalently bonded with the pendant vinyl functionality of the adherent silane, the graft polymer simultaneously formed and bonded to the pendant vinyl functionality by free radical reaction initiated by an oxidizing metal with at least one ethylenically unsaturated monomer selected from the group consisting of acrylamide and acrylic acid; and
   (c) a biomolecule covalently attached to the graft polymer.

8. The endoprosthesis of claim 7, wherein the biomolecule is covalently attached by means of an amine spacer.

9. The endoprosthesis of claim 8, wherein the amine spacer is a crosslinked polyalkyeneimine.

10. The endoprosthesis as in claim 7, in which the silane is trichlorovinylsilane.

11. The endoprosthesis of claim 7, wherein the biomolecule comprises an antithrombotic agent.

12. The endoprosthesis of claim 11, wherein the antithrombotic is selected from the group consisting of heparin and heparin derivatives.

* * * * *